(12) United States Patent
Tanaka et al.

(10) Patent No.: US 7,914,501 B2
(45) Date of Patent: Mar. 29, 2011

(54) INDWELLING NEEDLE

(75) Inventors: Shigeki Tanaka, Osaka (JP); Yosiharu Iwase, Tokyo (JP)

(73) Assignee: Nipro Corporation, Osaka-shi, Osaka (JP)

( * ) Notice: Subject to any disclaimer, the term of this patent is extended or adjusted under 35 U.S.C. 154(b) by 0 days.

(21) Appl. No.: 11/650,334

(22) Filed: Jan. 5, 2007

(65) Prior Publication Data
US 2008/0167619 A1 Jul. 10, 2008

(51) Int. Cl.
*A61M 5/32* (2006.01)
*A61M 5/178* (2006.01)

(52) U.S. Cl. .................. 604/198; 604/161; 604/164.08

(58) Field of Classification Search .................. 604/198, 604/164.08, 177, 264, 533–535, 110, 161
See application file for complete search history.

(56) References Cited

U.S. PATENT DOCUMENTS

| | | | | |
|---|---|---|---|---|
| 5,360,408 | A * | 11/1994 | Vaillancourt | 604/198 |
| 2002/0120215 | A1* | 8/2002 | Crawford et al. | 600/573 |
| 2004/0044313 | A1* | 3/2004 | Nakajima | 604/167.02 |
| 2005/0096599 | A1* | 5/2005 | Crawford et al. | 604/198 |
| 2007/0185456 | A1* | 8/2007 | Nakajima | 604/164.08 |

FOREIGN PATENT DOCUMENTS

| | | | |
|---|---|---|---|
| EP | 1201261 | A2 * | 5/2002 |
| EP | 1374942 | A1 * | 1/2004 |
| EP | 1475124 | A1 * | 11/2004 |
| JP | 10-085333 | | 4/1998 |
| JP | 2002-330945 | | 11/2002 |
| JP | 2003-180829 | | 7/2003 |

* cited by examiner

*Primary Examiner* — Kevin C Sirmons
*Assistant Examiner* — Bradley J Osinski
(74) *Attorney, Agent, or Firm* — Flynn, Thiel, Boutell & Tanis, P.C.

(57) ABSTRACT

Indwelling needle includes a cylindrical body, a needle having a sharp edge at a tip thereof, a cylindrical hub retaining proximal end of needle and moveable along main body, a protective cover moveable along main body and projecting from main body, and a spring elastically installed between hub and protective cover. First engaging portion of actuating lever is provided on body engaged with first projection of protective cover and second through-hole in hub to allow first retention mechanism to retain indwelling needle in a use state. First engaging portion is moved upward to release first retention mechanism. This separates protective cover and hub from each other under elastic force of spring. Protective cover and hub are thus retained in a housed state by second retention mechanism and third retention mechanism, respectively. This configuration reduces length of member contacting patient in the use state.

10 Claims, 4 Drawing Sheets

INDWELLING NEEDLE

BACKGROUND OF THE INVENTION

1. Field of the Invention

The present invention relates to an indwelling needle, and specifically, to an indwelling needle comprising a needle housed in a protective cover in a housed state.

2. Description of the Related Art

Currently a puncture is made in a patient with an indwelling needle for an intravenous drip infusion, dialysis, or the like. In this case, it is necessary to prevent the indwelling needle removed from the patent from accidentally sticking in a healthcare professional.

Thus, known indwelling needles comprise a needle having a sharp edge formed at its tip, a cylindrical hub at a proximal end of the needle, and a cylindrical protective cover that can be advanced and retracted along the needle (Patent Documents 1-3).

The indwelling needle in Patent Document 1 (Japanese Patent Laid-Open No. 10-85333) is composed of a hub that retains a proximal end of a cannula and a retention cylinder in which the hub is housed and held. The retention cylinder is advanced and retracted to house the cannula in the retention cylinder.

The indwelling needle in Patent Document 2 (Japanese Patent Laid-Open No. 2002-330945) is composed of a hub provided at a proximal end of a needle cannula and a safety shield that slidably houses the hub. In a use state, operating an actuator advances a spring elastically installed between the hub and the safety shield to house the safety shield in the needle cannula.

The indwelling needle in Patent Document 3 (Japanese Patent Laid-Open No. 2003-180829) is composed of a needle assembly made up of a needle cannula and a needle hub and a body portion that houses the needle assembly so that the needle assembly can be advanced and retracted. After the medical treatment is finished, a sticking element is stored in the body portion under the elastic force of a spring with operating an actuation button.

Thus, by using the indwelling needles in Patent Documents 1-3, after use, the above accident is prevented by storing the needle in the protective cover to establish a housed state.

However, the indwelling needles in Patent Documents 1-3 need to make the protective cover which is longer than a part of the needle projecting from the protective cover. This results in an unavoidable increase in the length of a member fixed to the patient in a use state.

In this case, for example, for a patient under a dialysis treatment, repeatedly making a puncture with the needle causes the tissue in the punctured part to be hardened, resulting in a lump-like swelling. Then, the long member fixed to the patient in the use state may come into contact with the swelling to cause the needle to be inserted into the vessel at an inappropriate angle. As a result, the patient expresses pain.

SUMMARY OF THE INVENTION

In view of these problems, an object of the present invention is to provide an indwelling needle having a shorter member that is fixed to an attaching object in the use state.

In one embodiment, there is provided an indwelling needle comprising a needle having a sharp edge formed at a tip thereof, a cylindrical hub that retains the needle, and a cylindrical protective cover which surrounds the needle and which is slidable along the needle. Further, the indwelling needle is switchable between a use state in which relative movement of the protective cover to a proximal end of the needle is caused to project the sharp edge of the needle from the protective cover and a housed state in which relative movement of the protective cover to a tip of the needle is caused to house the sharp edge of the needle in the protective cover. Specifically, a cylindrical body portion slidably retains the hub and protective cover and is fixed to an attaching object; a spring is elastically installed between the hub and the protective cover; and an actuating lever compresses the spring to move the hub and protective cover closer to each other to maintain the use state. In addition, in the use state, the lever is actuated causing relative movement of the hub and protective cover away from each other under the elastic force of the spring thereby housing the sharp edge of the needle in the protective cover and establishing the housed state.

In another embodiment, there is provided an indwelling needle comprising a needle having a sharp edge formed at a tip thereof, a cylindrical hub that retains the needle, and a cylindrical protective cover which surrounds the needle and which is slidable along the needle.

In particular, a cylindrical body slidably retains the hub and protective cover; a spring is elastically installed between the hub provided at a proximal end of the body and a protective cover provided at a distal end of the body; the spring biasing the hub and protective cover toward the proximal end and distal end, respectively, and away from each other; a first retention mechanism sets the spring in a compressed state thereby retaining the hub and protective cover closer to each other; and a second retention mechanism sets the spring in an extended state thereby retaining the protective cover subjected to the relative movement to the distal end of the body, at the distal end of the body, and a third retention mechanism retains the hub subjected to the relative movement to the proximal end of the body, at the proximal end of the body.

BRIEF DESCRIPTION OF THE DRAWINGS

FIG. 1 is a diagram showing a use state of an indwelling needle in accordance with a first embodiment, wherein FIG. 1(a) is a sectional view of the indwelling needle as viewed from the side and FIG. 1(b) is a sectional view of the indwelling needle as viewed from above;

FIG. 2 is a diagram showing a housed state of an indwelling needle in accordance with the first embodiment, wherein FIG. 2(a) is a sectional view of the indwelling needle as viewed from the side and FIG. 2(b) is a sectional view of the indwelling needle as viewed from above;

FIG. 3 is a diagram showing a use state of an indwelling needle in accordance with a second embodiment, wherein FIG. 3(a) is a sectional view of the indwelling needle as viewed from the side and FIG. 3(b) is a sectional view of the indwelling needle as viewed from above; and FIG. 4 is a diagram showing a housed state of an indwelling needle in accordance with the second embodiment, wherein FIG. 4(a) is a sectional view of the indwelling needle as viewed from the side and FIG. 4(b) is a sectional view of the indwelling needle as viewed from above.

DETAILED DESCRIPTION OF THE PREFERRED EMBODIMENTS

Figure 1:
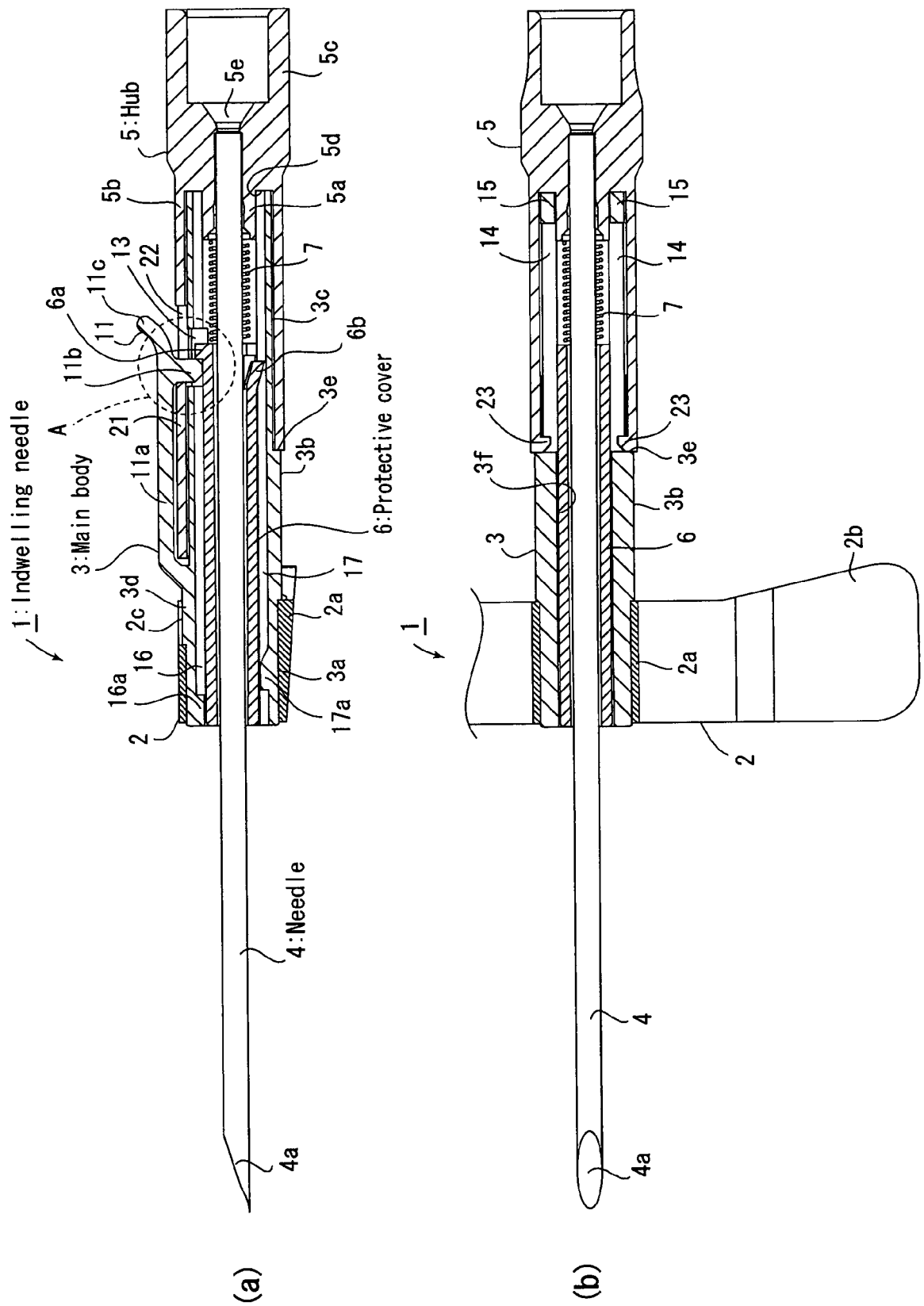
Figure 2:
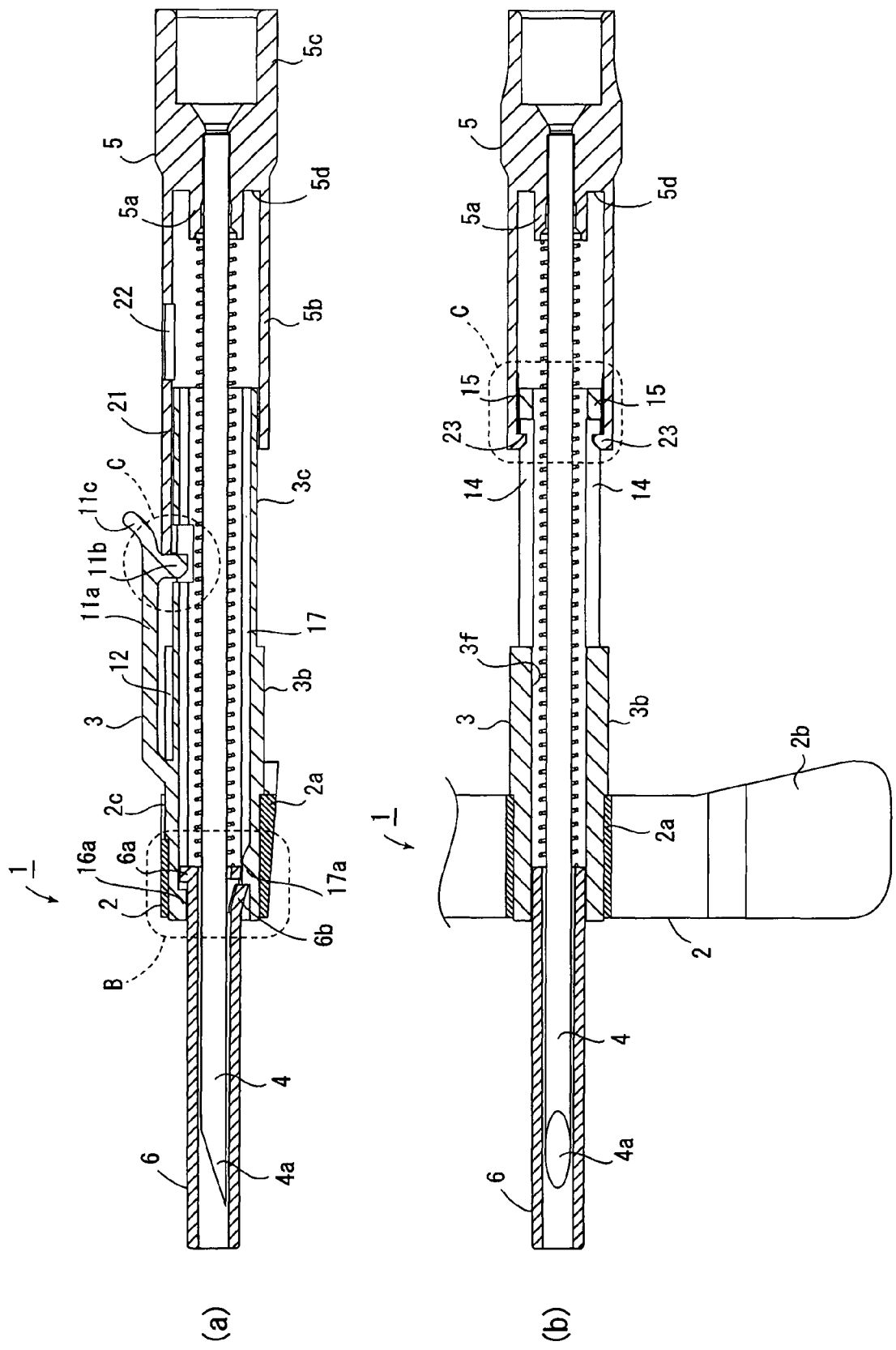

Embodiments will be described below. FIGS. 1 and 2 show an indwelling needle 1. FIG. 1 is a sectional view of a use state of the indwelling needle 1. FIG. 2 is a sectional view of a housed state of the indwelling needle 1. FIGS. 1(a) and 2(a) are sectional views of the indwelling needle 1 as viewed from the side. FIGS. 1(b) and 2(b) are sectional views of the indwelling needle 1 as viewed from above. In the description below, a sharp edge 4a of the needle 4 corresponds to a distal end.

The indwelling needle 1 is composed of a wing-shaped member 2 that is fixed to a patient as an attaching object, a cylindrical body 3 that is fixed to the patient via the wing-shaped member 2, a hollow needle 4 having a sharp edge 4a formed at a tip thereof, a cylindrical hub 5 which retains a proximal end of the needle 4 and which slides at a proximal end of the main body 3, a cylindrical protective cover 6 that slides at a distal end of the main body 3, and a spring 7 elastically installed between the hub 5 and the protective cover 6.

In a use state of the indwelling needle 1, the needle 4 projects from the distal end of the main body 3, with the protective cover 6 accommodated in the main body 3. In the use state, a puncture is made in the patient with the sharp edge 4a of the needle 4. Then, the main body 3, including the wing-shaped member 2, is fixed to the patient with a adhesive tape or the like.

On the other hand, in a housed state of the indwelling needle 1, the protective cover 6 is projected from the main body 3, and the needle 4 is housed in the protective cover 6. When transfusion to the patient or the like is finished, the needle 4 is housed in the protective cover 6 to prevent the sharp edge 4a from accidentally sticking in a healthcare professional.

The indwelling needle 1 in accordance with the present embodiment 1 further comprises a first retention mechanism A that maintains the main body 3, hub 5, and protective cover 6 in the use state, a second retention mechanism B that maintains the main body 3 and protective cover 6 in the housed state, and a third retention mechanism C that maintains the main body 3 and hub 5 in the housed state.

The wing-shaped member 2 is composed of a cylindrical portion 2a that surrounds the main body 3 and a wing portion 2b that extends from the cylindrical portion 2a in the opposite directions. A groove 2c is formed at the top (the upper part in FIG. 1(a)) of the cylindrical portion 2a to prevent rotation.

The indwelling needle 1 is fixed to wing portion 2b by deforming the wing portion 2b along the patient's skin and fixing the wing portion 2b to the skin from the surface of the wing-shaped member 2 with a adhesive tape.

The main body 3 is substantially cylindrical and has, on its outer peripheral surface, a connecting part 3a around which the cylindrical portion 2a of the wing-shaped member 2 is fitted, a larger diameter portion 3b located at a proximal end of the connecting part 3a, and a smaller diameter portion 3c located at a proximal end of the larger diameter portion 3b and around which the hub 5 is fitted. An actuating lever 11 is provided on the large diameter portion 3b.

The connecting part 3a is manufactured to the inner diameter of cylindrical portion 2a of the wing-shaped member 2. A projecting shape 3d that is fitted into the groove 2c in the cylindrical portion 2a is formed at the top of the connecting part 3a. This prevents relative rotation of the wing-shaped member 2 and the main body 3.

A step 3e is formed at the boundary between the larger diameter portion 3b and a smaller diameter portion 3c. Moreover, a keyway 12 (see FIG. 2(a)) is formed at the top of the larger diameter portion 3b so as to extend in the lateral direction of the figure.

The smaller diameter portion 3c is manufactured to have a diameter with which the smaller diameter portion 3c is slidable along an inner peripheral surface of the hub 5. The smaller diameter portion 3c has a first through-hole 13 formed at its top at a prescribed position and first guide holes 14 formed on the respective sides thereof so as to extend in the lateral direction of the figure. A fourth engaging portion 15 is formed at a proximal end of each first guide hole 14.

Further, a first guide groove 16 is formed at the top of inner peripheral surface 3f of the main body 3. A second engaging portion 16a projecting toward an inner periphery of the needle is formed at a distal end of the first guide groove 16.

Moreover, a second guide groove 17 is formed at the bottom of the inner peripheral surface 3f so as to extend from the distal end to proximal end of the inner peripheral surface 3f. The second guide groove 17 has a third engaging portion 17a formed at a position closer to its proximal end than the second engaging portion 16a. An inclined surface is formed at a proximal end of the third engaging portion 17a.

The actuating lever 11 is composed of an arm 11a having a distal end fixed to the larger diameter portion 3b, a first engaging portion 11b disposed at a proximal end of the arm 11a so as to penetrate the first through-hole 13, and a tab 11c disposed closer to a proximal end thereof than the first engaging portion 11b.

The arm 11a is elastically deformed so as to normally keep the first engaging portion 11b housed in the first through-hole 13. Raising the tab 11c upward to elastically deform the arm 11a enables the first engaging portion 11b to leave the through-hole 13.

The hub 5 is composed of a retaining portion 5a that retains the proximal end of the needle 4, a cylindrical portion 5b that houses the main body 3, and a connecting part 5c to which a infusion tube (not shown) is coupled. An annular groove 5d is formed between the retaining portion 5a and the cylindrical portion 5b.

The retaining portion 5a forms a spring receiving portion that fittingly retains the proximal end of the needle 4 and which abuts against the spring 7, which surrounds the needle 4.

Moreover, a liquid passage 5e is formed between the retaining portion 5a and the connecting part 5c so that a transfusion solution flowing in via the infusion tube is fed to the needle 4 through the liquid passage 5e.

A key shape 21 that engages with the keyway 12 in the main body 3 is provided at the top of the cylindrical portion 5b so as to project toward the distal end of the cylindrical portion 5b. A second through-hole 22 is formed at a proximal end of the key shape portion 21.

In the use state, shown in FIG. 1(a), the second through-hole 22 is located over the first through-hole 13 in the main body 3, and the first engaging portion 11b of the actuating lever 11 is inserted into the through-holes 22 and 13.

Third projection 23 projecting toward the inner periphery of the needle are formed on the respective sides of the cylindrical portion 5b at its distal end. Each of the third projection 23 moves along the first guide hole 14 in the main body 3 and prevents relative rotation of the hub 5 and the main body 3.

The protective cover 6 is slidably housed in the inner peripheral surface 3f of the main body 3 so that in the use state, its distal end aligns with the distal end of the main body 3.

A first projection 6a is formed at the top of the protective cover 6 so as to move along the first guide groove 16 in the main body 3. A second projection 6b is formed at the bottom of the protective cover 6 so as to move along the second guide groove 17 in the main body 3.

The second projection 6b is inclined from its distal end to proximal end. Upon coming into contact with the inclined surface of the third engaging portion 17a, formed on the second guide groove 17, the second projection 6b is elastically deformed toward the inner periphery of the protective cover 6. After climbing over the third engaging portion 17a, the second projection 6b returns and projects again toward the outer periphery of the protective cover 6.

The first and second projections 6a and 6b are then engaged with the first and second guide grooves 16 and 17 to prevent relative rotation of the protective cover 6 and body 3.

Now, description will be given of the first retention mechanism A that maintains the indwelling needle 1 in the use state. In FIG. 1, the hub 5 and protective cover 6 are retained close to each other against the elastic force of the spring 7.

In this state, the hub 5 is located on its foremost side with respect to the main body 3. The distal end of the cylindrical portion 5b abuts against the step 3e of the main body 3. The proximal end of the main body 3 is housed in the annular groove 5d in the hub 5.

The first engaging portion 11b of the actuating lever 11 is inserted into the second through-hole 22 in the hub 5. A distal end surface of the first engaging portion 11b thus engages with a distal end surface of the second through-hole 22. This prevents the hub 5 from moving toward its proximal end against the elastic force of the spring 7.

On the other hand, the protective cover 6 is located on its rearmost side with respect to the body. At this time, the distal end of the protective cover 6 substantially aligns with the distal end of the main body 3. Moreover, the first projection 6a is located closer to the proximal end of the body than the first engaging portion 11b of the actuating lever 11.

A distal end surface of the first projection 6a engages with a proximal end surface of the first engaging portion 11b. This prevents the protective cover 6 from moving toward its distal end side against the elastic force of the spring 7.

Thus, the indwelling needle 1 can be maintained in the use state by engaging the second through-hole 22 in the hub 5 and the first projection 6a on the protective cover 6 with the first engaging portion 11b of the actuating lever 11.

Next, with reference to FIG. 2, description will be given of the second retention mechanism B which maintains the main body 3 and the protective cover 6 in the housed state. When the first retention mechanism A is released from the state of the use state in FIG. 1, the hub 5 and the protective cover 6 are biased away from each other under the elastic force of the spring 7.

The protective cover 6 moves to its distal end side relative to the main body 3. The first projection 6a moves along the first guide groove 16 formed in the inner peripheral surface 3f of the main body 3.

The distal end surface of the first projection 6a engages with a proximal end surface of the second engaging portion 16a of the first guide groove 16. This prevents the protective cover 6 from moving toward its distal end side and falling from the main body 3.

On the other hand, moving the protective cover 6 to its distal end side relative to the main body 3 also moves the second projection 6b along the second guide groove 17 in the main body 3. Upon coming into contact with the inclined surface of the third engaging portion 17a, the second projection 6b is elastically deformed toward the inside of the protective cover 6. After that, when the second projection 6b passes over the third engaging portion 17a, the second projection 6b returns to its original shape.

Thus, the proximal end surface of the second projection 6b engages with a distal end surface of the third engaging portion 17a. This prevents the protective cover 6 from moving toward its proximal end side to return the needle to the use state.

As described above, the protective cover 6 and the main body 3 can be maintained in the housed state by engaging the first projection 6a and second projection 6b, formed on the protective cover 6, with the second and third engaging portions 16a and 17a, respectively, formed on the main body 3.

Next, description will be given of the third retention mechanism C which maintains the main body 3 and the hub 5 in the housed state. When the first retention mechanism A is released from the state of the use state in FIG. 1, the hub 5 and the protective cover 6 are biased away from each other under the elastic force of the spring 7.

The hub 5 moves to its distal end side relative to the main body 3. The third projection 23 on the cylindrical portion 3b moves along the first guide hole 14 in the main body 3. Then, the distal end surface of the third projection 23 engages with a distal end surface of the fourth engaging portion 15 located at the proximal end of the first guide hole 14. This prevents the hub 5 from moving toward its distal end side and falling from the main body 3.

On the other hand, by the relative movement of the hub 5 to its proximal end side by means of the spring 7, the first engaging portion 11b of the actuating lever 11 is housed in the first through-hole 13 in the main body 3 again.

At this time, the proximal end surface of the first engaging portion 11b engages with a distal end surface of the key shape portion 21 of the hub 5. This prevents the hub 5 from moving toward its distal end side to return the needle to the use state.

As described above, the hub 5 and the main body 3 can be maintained in the housed state by engaging the third projection 23 of the hub 5 with the fourth engaging portion 15 of the main body 3 and contacting the distal end of the key shape portion 21 of the hub 5 against the first engaging portion 11b of the actuating lever 11.

Description will be given of a method for using the indwelling needle 1 in accordance with the present embodiment configured as described above.

First, the indwelling needle 1 is adapted to be used in the use state, and the infusion tube is preconnected to the connecting part 5c of the hub 5. Further, the outer periphery of the needle 4 is covered by a cover (not shown) until a puncture is made in the patient with the needle 4.

Then, the cover is removed, the needle 4 is stuck into the patient's vessel, and the wing-shaped member 2 is deformed with following the patient's skin. Then, the wing-shaped member 2 is fixed to the patient with a tape or the like to fix the indwelling needle 1 to the patient.

Subsequently, a transfusion solution from the infusion tube is dispensed to the patient via the liquid passage 5e formed in the hub 5, and via the needle 4. When the transfusion is finished, the tape fixing the wing-shaped member 2 is first removed and the tab 11c of the actuating lever 11 is then raised without removing the needle from the patient.

The first engaging portion 11b leaves the first through-hole 13 of the main body 3 and the second through-hole 22 of the hub 5 by the elastic deformation of the arm 11a of the actuating lever 11, the first retention mechanism A maintaining the use state is released.

Releasing the first retention mechanism A causes relative movement of the hub 5 and protective cover 6 away from each other under the elastic force of the spring 7. With the arm 11a of the actuating lever 11 remaining elastically deformed, the first engaging portion 11b slides on the surface of the key shape portion 21 of the hub 5.

By moving of the hub 5 to the proximal end side relative to the main body 3 under the elastic force of the spring 7, the needle 4 moves to the proximal end side relative to the main body 3. Consequently, the needle 4 is pulled out of the patient's vessel. At this time, the needle 4 need not be completely pulled out of the vessel.

The hub 5 moves to its distal end relative to the main body 3, the arm 11a recovers from the elastic deformation. The first engaging portion 11b is thus housed in the first through-hole 13.

As a result, the first engaging portion 11b engages with the key shape portion 21 of the hub 5, while the third projection 23 simultaneously engages with the fourth engaging portion 15 of the main body 3. This allows the third retention mechanism C to maintain the housed state of the hub 5 and the main body 3.

On the other hand, when the protective cover 6 moves to its distal end side and then to its foremost position relative to the main body 3 under the elastic force of the spring 7, the first projection 6a of the protective cover 6 engages with the second engaging portion 16a formed in the first guide groove 16 in the main body 3, the second projection 6b engages with the third engaging portion 17a, formed in the second guide groove 17.

Thus, the sharp edge 4a of the needle 4 is housed in the protective cover 6. The second retention mechanism B maintains the housed state of the protective cover 6 and the main body 3.

The indwelling needle 1 in accordance with the present embodiment configured as described above, by switching the indwelling needle 1 from use state to housed state with the needle 4 to be housed in the protective cover 6, prevents from accidentally sticking of the needle 4 into a healthcare professional.

Further, the indwelling needle 1 in accordance with the present embodiment can be reduced in the length of its part which contacts the patient in the use state.

Specifically, in the use state, the hub 5 is located on its distal end side with respect to the main body 3. This makes it possible to increase the length of part of the needle 4 which projects from the distal end of the main body 3 to limit the part contacting the patient to the main body 3 and the connecting part 5c of the hub 5.

In the housed state, the hub 5 moves to its proximal end side relative to the main body 3 to expose the cylindrical portion 5b of the hub from the body. This increases the length of the part contacting the patient, but the housed state ends when the indwelling needle 1 is removed from the patient. This precludes a strain on the patient.

Moreover, the indwelling needle 1 in accordance with the present embodiment can prevent the patient's vessel from being damaged when the use state is switched to the housed state. The indwelling needle 1 in accordance with the present embodiment can also prevent the possible splashing of blood.

Specifically, switching the use state to the housed state positions the hub 5 on its proximal end side with respect to the main body 3. This causes relative movement of the protective cover 6 to its distal end side such that the needle 4 subjected to relative movement to its proximal end side is housed in the protective cover 6. Thus, part of the needle 4 projecting from the main body 3 is pulled out of the vessel and the needle 4 is housed in the protective cover 6 with the state remaining unchanged. This precludes a strain on the vessel and suppresses the possible splashing of blood.

In contrast, with the conventional indwelling needles in Patent Documents 1-3, the entire needle projecting from the protective cover is housed in the protective cover at a time. This may damage the vessel or splash the blood in the needle.

Figure 3:
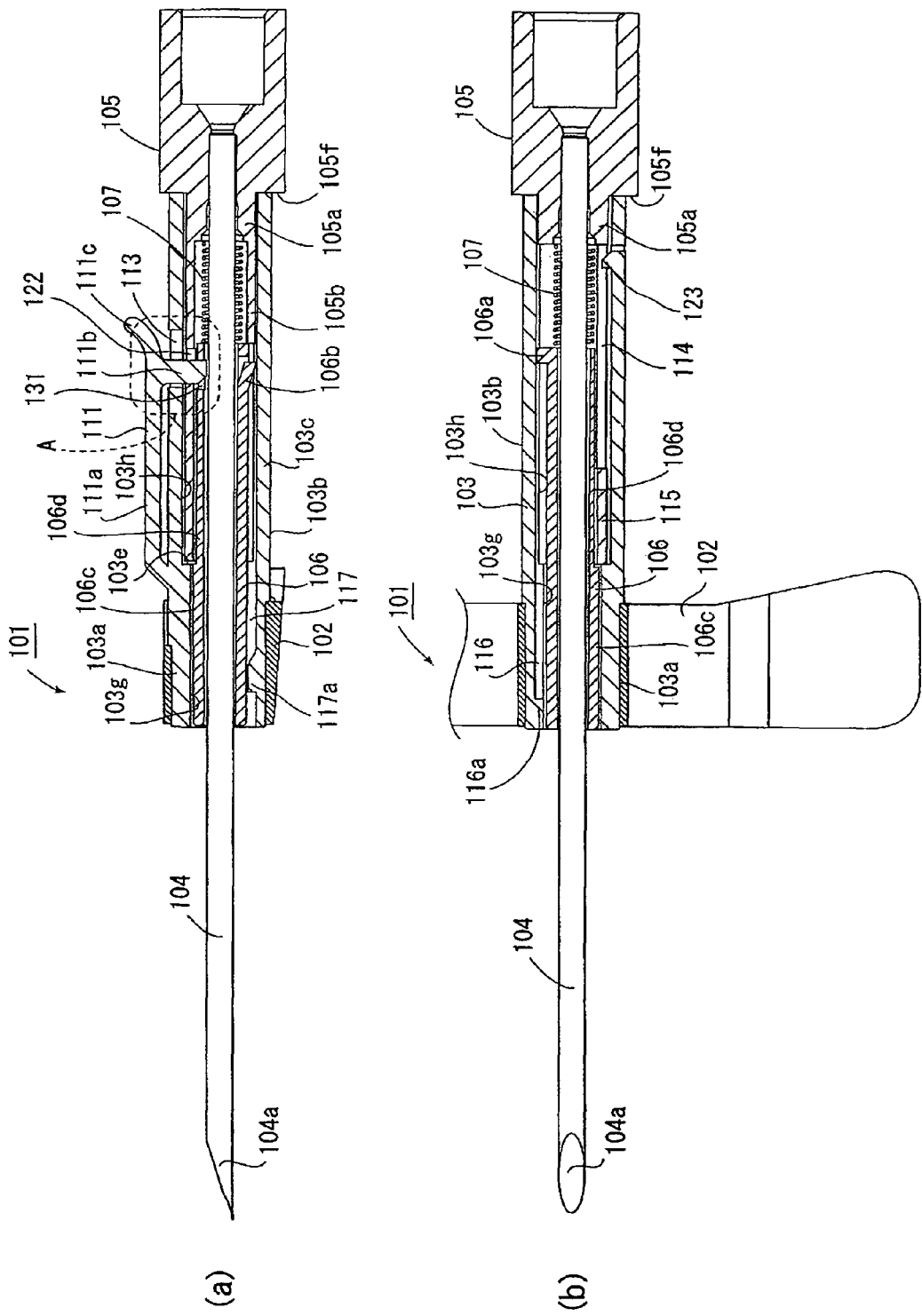
Figure 4:
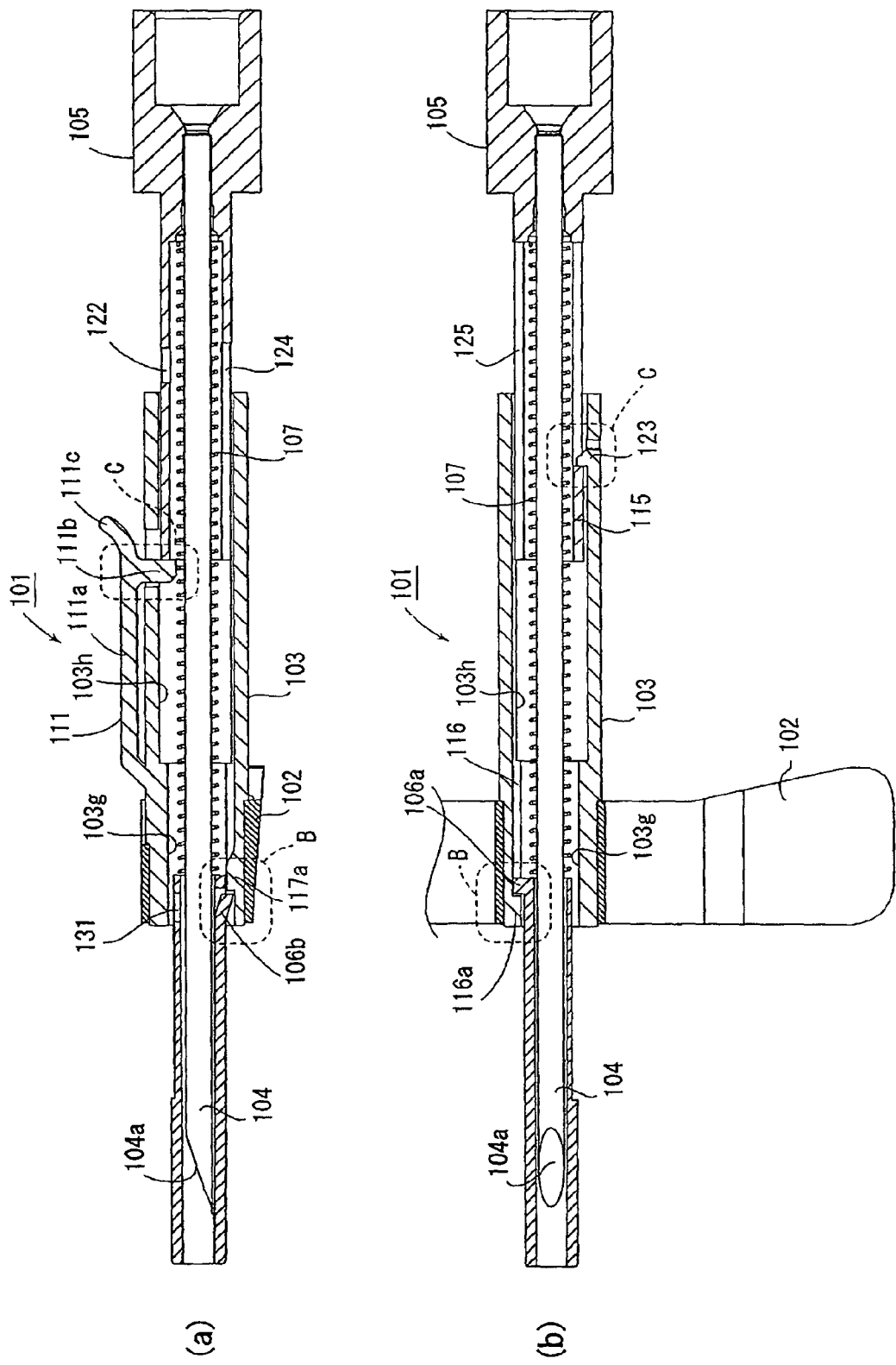

Now, a second embodiment of the present invention will be described with reference to FIGS. 3 and 4. The present embodiment has a configuration similar to that of the first embodiment. In the description below, members having the same functions as those in the first embodiment have the same name as the corresponding members of the first embodiment. The reference numeral of each of the members of the second embodiment corresponds to that of the corresponding member of the first embodiment plus 100.

The indwelling needle 101 in accordance with the present embodiment is composed of a wing-shaped member 102 that is fixed to a patient, a cylindrical body 103 retained by the wing-shaped member 102, a hollow needle 104 having a sharp edge 104a formed at a tip thereof, a cylindrical hub 105 which retains a proximal end of the needle 104 and which advances and retracts along the body 103, a protective cover 106 which advances and retracts along the body 103 and which can project to the leftward, in the figure, from the body 103, and a spring 107 elastically installed between the hub 105 and the protective cover 106.

The indwelling needle 101 further comprises a first retention mechanism A that maintains the body 103, hub 105, and protective cover 106 in the use state, a second retention mechanism B that maintains the body 103 and protective cover 106 in the housed state, and a third retention mechanism C that maintains the body 103 and hub 105 in the housed state.

The body 103 is adapted to slidably retain the hub 105 and the protective cover 106 therein in the use state, and has an outer peripheral surface composed of a connecting part 105c to which the wing-shaped member 102 is coupled and a larger diameter portion 103b formed on a proximal end side of the connecting part. An actuating lever 111 is provided on the large diameter portion 103b.

A first through-hole 113 is holed at the top of the larger diameter portion 103 at a prescribed position. A third projection 123 projects to the inward from one side (the lower part in FIG. 3(b)) of proximal end of the larger diameter portion 103b.

The body 103 has a smaller diameter portion 103g formed at its distal end to slidably retain the protective cover 106 and a larger diameter portion 103h formed on a proximal end side of the smaller diameter portion 103g to slidably retain the hub 105. A step 103e is formed at the boundary between the smaller diameter portion 103g and the larger diameter portion 103h.

A first guide groove 116 having a second engaging portion 116a formed from its distal end to proximal end is formed in one side (the upper part in FIG. 3(b)) of inner peripheral surface 103f of the body 103. A second guide groove 117 having a third engaging portion 117a formed from its distal end to proximal end is formed at the bottom of the inner peripheral surface 103f.

The actuating lever 111 comprises an arm 111a, a first connecting part 111b, and a tab 111c. The first engaging portion 111b penetrates the first through-hole 113.

The hub 105 is composed of a retaining portion 105a that retains the needle 104, a cylindrical portion 105b that advances and retracts through the larger diameter portion 103b of the body 103, and a connecting part 105c to which a infusion tube is coupled. A spring bearing is formed on the inner periphery of cylindrical portion 105b. A step 105f is formed around the outer periphery of the cylindrical portion 105b; the proximal end of the body 103 abuts against the step 105f.

The cylindrical portion 105b has a second through-hole 122 at its top and a first guide hole 114 formed in one side thereof (the lower part in FIG. 3(b)) in the lateral direction of the figure and with which the third projection 123 of the body 103 engages.

Further, a fourth guide groove 124 is formed at the bottom of inner peripheral surface of the cylindrical portion 105b at a position where the fourth guide groove 124 aligns with the second guide groove 117 in the body 103 in the use state. Moreover, a fifth guide groove 125 is formed on the other side of the first guide hole 114 at a position where the fifth guide groove 125 aligns with the first guide groove 116 in the body 103 in the use state.

The protective cover 106 is composed of a larger diameter portion 106c that slides through the smaller diameter portion 103c of the main body 103 in the use state and a smaller diameter portion 106d that slides through the cylindrical portion 105b of the hub 105 in the use state. The spring 107 is elastically installed between the proximal end of the smaller diameter portion 106d and the cylindrical portion 105b of the hub 105.

Further, the protective cover 106 has a first projection 106a formed on the proximal end of the side thereof, the first projection 106a moving along the first guide groove 116 in the body 103 and the fifth guide groove 125 in the hub 105 and leaving the fifth guide groove 125 in the housed state.

Moreover, the protective cover 106 has a second projection 106b formed at the proximal end of the bottom thereof, the second projection 106b moving along the second guide groove 117 in the body 103 and the fourth guide groove 124 in the hub 105 and leaving the fourth guide groove 124 in the housed state.

A third through-hole 131 is holed at the top of the smaller diameter portion 106d and aligns with the first through-hole 113 in the body 103 in the use state.

Description will be given of the first retention mechanism A which maintains the indwelling needle 101 in the use state. In FIG. 3(a), moving the hub 105 and protective cover 106 closer to each other against the elastic force of the spring 107 causes the distal end of cylindrical portion 105b of the hub 105 to abut against the step 103e of the body 103. At the same time, the proximal end of the body 103 abuts against the step 105f of the hub 105.

At this time, the first through-hole 113 in the body 103, the second through-hole 122 in the hub 105, and the third through-hole 131 in the protective cover 106 align with one another. The first projection 106a of the actuating lever 111 is the inserted into the through-holes 113, 122, and 131.

Then, a distal end surface of the first engaging portion 111b engages with a distal end surface of the second through-hole 122 in the hub 105 to prevent the hub 105 from moving toward its proximal end side.

At the same time, the first projection 106a is inserted into the third through-hole 131 to engage a proximal end surface of the first engaging portion 111b with a proximal end surface of the third through-hole 131 to prevent the hub 105 from moving toward its distal end side.

Thus, the indwelling needle 101 can be maintained in the use state by inserting the first engaging portion 111b of the actuating lever 111 into the second through-hole 122 in the hub 105 and into the third through-hole 131 in the protective cover 106.

Now, with reference to FIG. 4, description will be given of the second retention mechanism B, which maintains the body 103 and the protective cover 106 in the housed state. In the use state in FIG. 1, releasing the first retention mechanism A biases the hub 105 and the protective cover 106 away from each other under the elastic force of the spring 107.

The protective cover 106 moves to its distal end side relative to the body 103. The first projection 106a moves along the first guide groove 116 formed in the inner peripheral surface 103f of the body 103.

The distal end surface of the first projection 106a engages with a proximal end surface of the second engaging portion 116a of the first guide groove 116. This prevents the protective cover 106 from moving toward its distal end side and falling from the body 103.

On the other hand, moving the protective cover 106 to its distal end side relative to the body 103 also moves the second projection 106b along the second guide groove 117 in the body 103. Upon coming into contact with the inclined surface of the third engaging portion 117a, the second projection 106b is elastically deformed toward the inside of the protective cover 106. After the second projection 106b passes over the third engaging portion 117a, the second projection 106b returns to its original shape.

Thus, the distal end surface of the second projection 106b engages with a proximal end surface of the third engaging portion 117a. This prevents the protective cover 106 from moving toward its proximal end side to return the needle to the use state.

Thus, the protective cover 106 and the body 103 can be maintained in the housed state by engaging the first projection 106a and second projection 106b, formed on the protective cover 106, with the second and third engaging portion 116a and 117a, respectively, formed on the body 103.

Now, description will be given of the third retention mechanism C which maintains the body 103 and the hub 105 in the housed state. In the use state in FIG. 1, releasing the first retention mechanism A biases the hub 105 and the protective cover 106 away from each other under the elastic force of the spring 107.

The hub 105 moves to its distal end side relative to the body 103. The third projection 123 on the cylindrical portion 105b moves along the first guide hole 114 in the body 103. Then, the distal end surface of the third projection 123 engages with a distal end surface of the fourth engaging portion 115 located at the proximal end of the first guide hole 114. This prevents the hub 105 from moving toward its distal end side and falling from the body 103.

On the other hand, relative movement of the hub 105 to its proximal end side by means of the spring 107 allows the first engaging portion 111b of the actuating lever 111 to be housed in the first through-hole 113 in the body 103 again. At this time, the proximal end surface of the first engaging portion 111b engages with a distal end surface of cylindrical portion 105b of the hub 105. This prevents the hub 105 from moving toward its distal end side to return the needle to the use state.

Thus, the hub 105 and the body 103 can be maintained in the housed state by engaging the third projection 123 of the hub 105 with the fourth engaging portion 115 of the body 103 and abutting the distal end of the cylindrical portion 105b against the first engaging portion 111b of the actuating lever 111.

Also with the indwelling needle 101 in accordance with the second embodiment, operating the actuating lever 111 allows the indwelling needle 101 to be switched from the use state to the housed state, as is the case with the indwelling needle 101 in accordance with the first embodiment.

That is, in the use state, the member contacting the patient can be made shorter. In the housed state, the protective cover 106 can house the needle 104, preventing possible damage to the vessel and the possible splashing of blood.

What is claimed is:

1. An indwelling needle switchable between a use state and a housed state and defining a longitudinal axis, the indwelling needle comprising:

a needle having a proximal end and a sharp edge formed at the distal end thereof, a cylindrical hub that retains the needle, the cylindrical hub having an outer portion with an aperture therein, the cylindrical hub also having a hub interior, a cylindrical protective cover which surrounds and is slidable along the needle, the protective cover having a proximal and a distal end, and a radially outwardly extending projection adjacent the proximal end, a cylindrical body portion having an attachment member capable of fixing the body portion to a patient and having a body portion interior, the cylindrical body portion retaining the hub and the protective cover such that the hub and the protective cover are axially slidably movable relative to the body portion, the body portion comprising an engagement member shaped to be in sliding engagement with the projection of the protective cover, the engagement member having a proximal end, a spring that is elastically installed between the hub and the protective cover, and an actuating lever, attached to and extending at least partially outwardly from the cylindrical body portion, that compresses the spring to move the hub and protective cover closer to each other to maintain the use state, the actuating lever comprising an arm portion and an actuating engaging portion extending inwardly from the arm portion;

the housed state involving relative movement of the protective cover to a distal end of the needle and housing of the sharp edge of the needle in the protective cover and the proximal end of the engagement member engaging the projection of the protective cover to hold the protective cover in the housed state, the use state involving relative movement of the protective cover to a proximal end of the needle and projection of the sharp edge of the needle from the protective cover and from a distal end of the body portion by a predefined axial distance and a substantial portion of the protective cover being retained in the hub interior and the body portion interior, and operation of the actuating lever in the use state causing relative movement of the hub and protective cover away isolatedly from each other with respect to the body portion under the elastic force of the spring thereby housing the sharp edge of the needle in the protective cover and establishing the housed state, and operation of the actuating lever in the use state causing the protective cover to move distally relative to the body portion and the hub and the needle to move proximally relative to the body portion, by the spring, to position the sharp edge of the needle at an axial distance from the distal end of the body portion which is less than the predefined axial distance in the use state, wherein, to establish the use state, the actuating engaging portion of the actuating lever extends through the cylindrical hub aperture and engages the projection of the cylindrical protective cover and the engaging portion of the actuating lever in the use state is located closer to the proximal end of the needle than the distal end of the needle.

2. The indwelling needle according to claim 1, wherein a second projection projects from an outer periphery of the protective cover at a position different from that from which the first projection projects, and the body portion has a second engaging portion and a third engaging portion on an inner peripheral surface thereof, the second engaging portion abutting against the first projection of the protective cover, the third engaging portion engaging with the second projection, and to establish the housed state, a distal end surface of the first projection of the protective cover is abutted against a distal end surface of the second engaging portion of the body portion to retain and prevent the protective cover from falling from the body portion, and a proximal end surface of the second projection of the protective cover is abutted against a distal end surface of the third engaging portion of the body portion to retain and prevent the protective cover from returning to the use state.

3. The indwelling needle according to claim 2, wherein a third projection is provided on one of the hub and the body portion so as to project toward the other of the hub and the body portion, and a fourth engaging portion with which the third projection is engaged is provided on the other of the hub and the body portion, and to establish the housed state, a distal end surface of the hub is abutted against a proximal end surface of the first engaging portion of the actuating lever to retain and prevent the hub from returning to the use state, and the third projection and the fourth engaging portion are engaged with each other to retain and prevent the hub from falling from the body portion.

4. The indwelling needle according to claim 1, wherein the attachment member is a wing-shaped member.

5. An indwelling needle comprising a needle having a sharp edge formed at a tip thereof, a cylindrical hub that retains the needle, and a cylindrical protective cover which surrounds and is slidable along the needle, the indwelling needle being switchable between a use state in which relative movement of the protective cover to a proximal end of the needle causes the sharp edge of the needle to project from the protective cover, and a housed state in which relative movement of the protective cover to a distal end of the needle causes the sharp edge of the needle to be housed in the protective cover, the indwelling needle further comprising:

a cylindrical body portion fixed to a patient, the body portion having an outer surface and retaining the hub and the protective cover such that the hub and the protective cover are axially slidably movable relative to the body portion, a spring that is elastically installed between the hub and the protective cover, and an actuating lever that extends at least partially outwardly from the outer surface and that compresses the spring to move the hub and protective cover closer to each other to maintain the use state, wherein, in the use state, the actuating lever is operated to cause relative movement of the hub and protective cover away from each other under the elastic force of the spring to house the sharp edge of the needle in the protective cover to establish the housed state;

the hub comprises a cylindrical portion which houses the protective cover and in which a through-hole is formed and a spring receiving portion positioned in the cylindrical portion and elastically contacted by the spring, the protective cover comprises a first projection that projects toward the cylindrical portion, and the actuating lever comprises a flexible arm fixed to the body portion at one end thereof and a first engaging portion that projects closer to the needle than the other end of the arm, and to establish the use state, the first engaging portion of the actuating lever is inserted into the through-hole in the hub, a distal end surface of the first engaging portion is engaged with a distal end surface of the through-hole, and the first projection of the protective cover is positioned closer to a proximal end of the indwelling needle than the distal end surface of the through-hole in the hub to engage a distal end surface of the first projection with a proximal end surface of the first engaging portion, and operation of the actuating lever in the use state causing the protective cover to move distally relative to the body portion and the hub and the needle to move proximally relative to the body portion, by the spring.

6. The indwelling needle according to claim 5,
wherein the hub comprises a cylindrical portion which houses the protective cover and in which a through-hole is formed and a spring receiving portion positioned in the cylindrical portion and elastically contacted by the spring, the protective cover comprises a first projection that projects toward the cylindrical portion, and the actuating lever comprises a flexible arm fixed to the body portion at a first end and having a free end at a second end and a first engaging portion that projects closer to the needle than the second end of the arm, and to establish the use state,
the first engaging portion of the actuating lever is inserted into the through-hole in the hub, a distal end surface of the first engaging portion is engaged with a distal end surface of the through-hole, and the first projection of the protective cover is positioned closer to a proximal end of the indwelling needle than the distal end surface of the through-hole in the hub to engage a distal end surface of the first projection with a proximal end surface of the first engaging portion; and wherein the hub slidably retains the body portion in the cylindrical portion, a third projection is provided on one of the hub and the body portion so as to project toward the other of the hub and the body portion, and a fourth engaging portion with which the third projection is engaged is provided on the other of the hub and the body portion, and to establish the housed state,
a distal end surface of the hub is abutted against a proximal end surface of the first engaging portion of the actuating lever to retain and prevent the hub from returning to the use state, and
the third projection and the fourth engaging portion are engaged with each other to retain and prevent the hub from falling from the body portion.

7. An indwelling needle defining a longitudinal axis and axially-spaced proximal and distal ends, said indwelling needle comprising:
a needle having a distal end defining a sharp edge for insertion into a patient and a proximal end spaced from said distal end;
a cylindrically-shaped hub in which said proximal end of said needle is fixed, said hub defining a radially-oriented opening therein;
a cylindrically-shaped protective cover disposed in surrounding relation with said needle and being slidably movable relative thereto;
a cylindrically-shaped body portion, said hub and said protective cover being retained within an interior of said body portion and being axially slidably movable relative to said body portion, said body portion having a member configured for attachment to a patient;
a biasing member disposed between said hub and said protective cover to bias said hub and said protective cover away from one another;
said indwelling needle having a housed state wherein said protective cover is positioned at and defines said distal end of said indwelling needle so as to house said sharp edge of said needle therein, and a use state wherein said protective cover is positioned adjacent said proximal end of said indwelling needle such that said sharp edge of said needle projects axially beyond said protective cover and axially beyond a distal end of said body portion by a predefined axial distance; and
an actuating lever disposed on said body portion and extending at least partially outwardly therefrom, said actuating lever being movable between first and second positions respectively corresponding to said use state and said housed state of said indwelling needle, said actuating lever in said first position being disposed to compress said biasing member and position said hub and said protective cover adjacent one another to maintain said use state of said indwelling needle, and said actuating lever in said first position being operable to cause movement of said hub and said needle relative to said body portion in a proximal direction under the biasing force of said biasing member to position said sharp edge of said needle at an axial distance from said distal end of said body portion which is less than said predefined axial distance in said use state, and movement of said protective cover relative to said body portion in a distal direction under the biasing force of said biasing member to house said sharp edge of said needle and establish said housed state of said indwelling needle, and said actuating lever comprising an arm which is movable relative to said body portion, said arm having one end fixed to said body portion and a free end axially spaced from said one end, said free end being engaged within said opening of said hub in said first position of said actuating lever.

8. The indwelling needle according to claim 7, wherein said hub has a portion which surrounds part of said protective cover.

9. The indwelling needle according to claim 7, wherein said hub has a proximal end and a distal end spaced axially therefrom and defining a distally-facing surface, said opening in said hub being disposed between said proximal and distal ends of said hub, said actuating lever in said first position corresponding to said use state engaging an edge of said hub defining a distal terminal extent of said opening and said actuating lever in said second position corresponding to said housed state being disengaged from said opening of said hub and engaged with said distally-facing surface of said hub.

10. The indwelling needle according to claim 7, wherein said body portion and said hub are separate and distinct components of said indwelling needle.

* * * * *